US006770800B2

(12) United States Patent
Gordon-Kamm et al.

(10) Patent No.: US 6,770,800 B2
(45) Date of Patent: *Aug. 3, 2004

(54) METHODS OF USING VIRAL REPLICASE POLYNUCLEOTIDES AND POLYPEPTIDES

(75) Inventors: William J. Gordon-Kamm, Urbandale, IA (US); Keith S. Lowe, Johnston, IA (US); Carolyn A. Gregory, Clive, IA (US); George J. Hoerster, Des Moines, IA (US); Brian A. Larkins, Tucson, AZ (US); Brian R. Dilkes, Tucson, AZ (US); Ronald Burnett, Bethlehem, PA (US)

(73) Assignees: Pioneer Hi-Bred International, Inc., Des Moines, IA (US); The Arizona Board of Regents on Behalf of the University of Arizona, Tucson, AZ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/511,445
(22) Filed: Feb. 22, 2000
(65) Prior Publication Data

US 2002/0112258 A1 Aug. 15, 2002

Related U.S. Application Data

(60) Provisional application No. 60/124,136, filed on Mar. 12, 1999.

(51) Int. Cl.[7] ............................ C12N 15/82; C12N 15/34
(52) U.S. Cl. ...................... 800/290; 800/280; 800/287; 800/288
(58) Field of Search .............................. 800/280, 287, 800/288, 290, 298; 435/468, 419; 536/23.72

(56) References Cited

U.S. PATENT DOCUMENTS

| | | | |
|---|---|---|---|
| 5,945,581 A | | 8/1999 | Zaitlin et al. ............... 800/301 |
| 5,986,175 A | | 11/1999 | Jilka et al. .................. 800/301 |
| 6,133,505 A | * | 10/2000 | Gronenborn ................ 800/280 |
| 6,284,947 B1 | * | 9/2001 | Gordon-Kamm et al. ... 800/290 |

FOREIGN PATENT DOCUMENTS

| | | | |
|---|---|---|---|
| WO | WO 91/13542 | 9/1991 | |
| WO | WO 97/47745 | 12/1997 | ........... C12N/15/29 |
| WO | WO 98/56811 | 12/1998 | ........... C07K/14/00 |

OTHER PUBLICATIONS

Larkins, et al "Investigating the hows and whys of DNA endoreduplication", 2001, Journal of Experimental Botany, vol. 52, No. 355 pp. 183–192.*
Xie et al., "Plant cells contain a novel member of the retinoblastoma family of growth regulatory proteins", *The EMBO Journal*, vol. 15, No. 18, pp. 4900–4908 (1996).
Xie et al., "Identification and analysis of a retinoblastoma binding motif in the replication protein of a plant DNA virus: requirement for efficient viral DNA replication", *The EMBO Journal*, vol. 14, No. 16, pp. 4073–4082 (1995).
Collin et al., "The Two Nonstructural Proteins from Wheat Dwarf Virus Involved in Viral Gene Expression and Replication are Retinoblastoma–Binding Proteins", *Virology*, vol. 219, pp. 324–329 (1996).
Grafi et al., "A maize cDNA encoding a member of the retinoblastoma protein family: Involvement in endoreduplication", *Proc. Natl. Acad. Sci. USA*, vol. 93, pp. 8962–8967 (1996).
Grafi, Gideon; "Cell Cycle Regulation of DNA Replication: The Endoreduplication Perspective", *Experimental Cell Research*, vol. 244, pp. 372–378 (1988).
Grafi et al., "Endoreduplication in Maize Endosperm: Involvement of M Phase–Promoting Factor Inhibition and Induction of S Phase–Related Kinases", *Science*, vol. 269, pp. 1262–1264 (1995).
Gutierrez, Crisanto; "The retinoblastoma pathway in plant cell cycle and development", *Current Opinion in Plant Biology*, vol. 1, No. 2, pp. 492–497 (1998).
Oritz et al., "Effect of the parthenocarpy gene $P_1$ and ploidy on fruit and bunch traits of plantain–banana hybrids" *Heredity* 75:460–465 (1995).
Orozco, B.M., "Functional Domains of a Geminivirus Replication Protein", *The Journal of Biological Chemistry* 272(15):9840–9846 (1997).
Stanley, J., "Geminiviruses: plant viral vectors", *Current Opinion in Genetics and Development* 3:91–96 (1993).
Timmermans et al., "Geminiviruses and Their Use as Extrachromosomal Replicons", *Annual Review Plant Physiol Plant Mol. Bio.* 45:79–112 (1994).
Warner et al., "Effects of Polyploidy on Photosynthetic Rates, Photosynthetic Enzymes, Contents of DNA, Chlorophyll, and Size and Numbers of Photosynthetic Cells in the $C_4$ Dicot Atriplex confertifolia[1]", *Plant Physiol.* 91:1143–1151 (1989).
Elmer et al., "Agrobacterium–mediated inoculation of plants with tomato golden mosaic virus DNAs", *Plant Mol. Biol.* 10:225–234 (1988).
Hanley–Bowdoin et al., "Functional Expression of the Leftward Open Reading Frames of the A Component of Tomato Golden Mosaic Virus in Transgenic Tobacco Plants", *The Plant Cell* 1:1057–1067 (1989).
Rogers et al., "Tomato Golden Mosaic Virus A Component DNA Replicates Autonomously in Transgenic Plants", *Cell* 45:583–600 (1986).

(List continued on next page.)

*Primary Examiner*—Elizabeth F. McElwain
*Assistant Examiner*—Cynthia Collins
(74) *Attorney, Agent, or Firm*—Pioneer Hi-Bred International, Inc.

(57) ABSTRACT

The invention provides novel methods of using viral replicase polypeptides and polynucleotides. Included are methods for modulating endoreduplication and increasing crop yield.

5 Claims, 1 Drawing Sheet

OTHER PUBLICATIONS van Dun et al., Expression of Alfalfa Mosaic Virus cDNA1 and 2 in Transgenic Tobacco Plants, *Virology* 163:572–578 (1988).

Brunori et al., "Cell number and polyploidy in the starchy endosperm of *Triticum aestivum* in relation to seed weight", *J. Genet. & Breed.* 47:217–220 (1993).

Caldeira et al., "Human papillomavirus E7 proteins stimulate proliferation independently of their ability to associate with retinoblastoma protein", Oncogene 19:821–826 (2000).

Chasan, R., "Geminiviruses: A Twin Approach to Replication", *The Plant Cell*, 2:659–660 (1995).

Davies et al., "The Structure, Expression, functions and Possible Exploitation of Geminivirus Genomes", *Plant DNA Infectious Agents*/edited by T. Hohn and J. Schell, Wien: Springer–Verlag 2:31–52 (1987).

Gendreau et al., "Cellular Basis of Hypocotyl Growth in *Arabidopsis thaliana*[1]", *Plant Physiol.* 114:295–305 (1997).

Iuliano et al., "Pivotal Role of the RB Family in in Vitro Thyroid Cell Transformation", *Experimental Cell Research* 260:257–267 (2000).

Kowles et al., "Endosperm Development in Maize", *International Review of Cytology* 112:97–136 (1988).

E. Morgan, "A region of SV40 Large T antigen can substitute for a transforming domain of the adenovirus E1A products", Nature 334:168–170 (1988).

Egelkrout et al., "Proliferating Cell Nuclear Antigen Transcription is Repressed Through and E2F Consensus Element and Activated by Geminivirus Infection in Mature Leaves", *The Plant Cell* 13:1437–1452 (2001).

Hanley–Bowdoin et al., "Expression of functional replication protein from tomato golden mosaic virus in transonic tobacco plants", *Proc. Natl. Acad. Sci. USA* 87:1446–1450 (1990).

Moran, Elizabeth, "Interaction of adenoviral proteins with pRB and p53", *The FASEB Journal* 7:880–885 (1993).

Nagar et al., "A geminivirus Induces Expression of a Hose DNA Synthesis Protein in Terminally Differentiated Plant Cells", *The Plant Cell* 7:705–719 (1995).

Vousden, Karen, "Interactions of human papillomavirus transforming proteins with the products of tumor suppressor genes", The FASEB Journal 7:872–879 (1993).

Ach et al., "*RRB1* and *RRB2* Encode Maize Retinoblastoma–Related Proteins That Interact with a Plant D–Type Cyclin and Geminivirus Replication Protein", *Mol. Cell Biol.* 17(19):5077–5086 (1977).

de Jager et al., "Retinoblastoma proteins in plants", *Plant Mol. Biol.* 41:295–299 (1999).

Palmer et al. "The Molecular Biology of Mastreviruses", *Advances in Virus Research* 50:183–233 (1998).

* cited by examiner

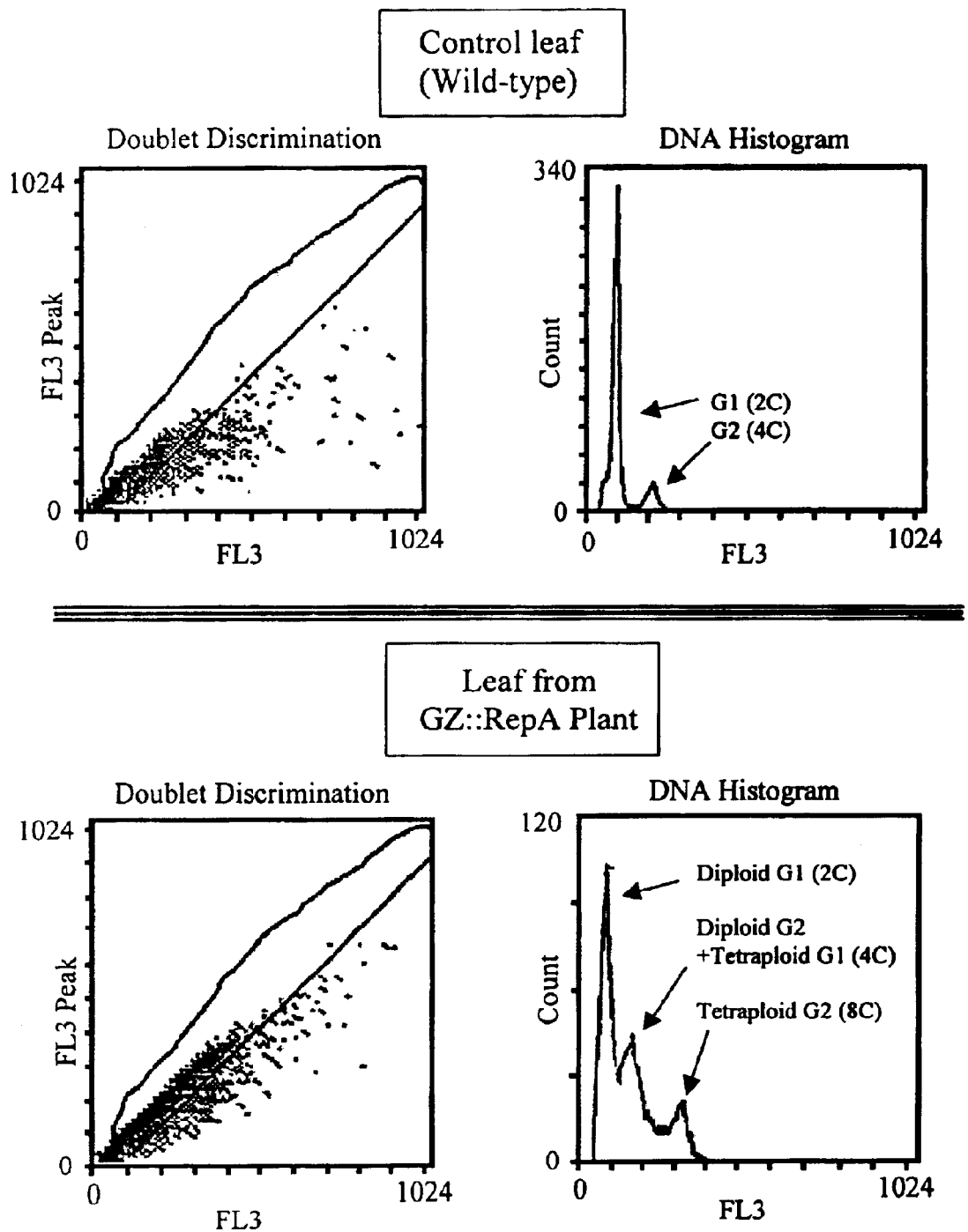
Figure I. Flow cytometric analysis of nuclei extracted from non-transformed Hi-II plant tissue (top) and from GZ::RepA-transformed plant tissue (bottom). Leaf tissue from approximately 1.5 meter tall regenerated plants was sampled for both treatments.

METHODS OF USING VIRAL REPLICASE POLYNUCLEOTIDES AND POLYPEPTIDES

CROSS-REFERENCE TO RELATED APPLICATIONS

This application claims priority under 35 USC 119 to U.S. Provisional Application Serial No. 60/124,136 filed Mar. 12, 1999 the disclosure of which is incorporated herein by reference.

TECHNICAL FIELD

The present invention relates generally to plant molecular biology.

BACKGROUND OF THE INVENTION

Cell division plays a crucial role during all phases of plant development. The continuation of organogenesis and growth responses to a changing environment requires precise spatial, temporal and developmental regulation of cell division activity in meristems (and in cells with the capability to form new meristems such as in lateral root formation). Such control of cell division is also important in organs themselves (i.e. separate from meristems per se), for example, in leaf expansion, secondary growth, and endoreduplication.

A complex network controls cell proliferation in eukaryotes. Various regulatory pathways communicate environmental constraints, such as nutrient availability, mitogenic signals such as growth factors or hormones, or developmental cues such as the transition from vegetative to reproductive. Ultimately, these regulatory pathways control the timing, frequency (rate), plane and position of cell divisions.

Plants have unique developmental features that distinguish them from other eukaryotes. Plant cells do not migrate, and thus only cell division, expansion and programmed cell death determine morphogenesis. Organs are formed throughout the entire life span of the plant from specialized regions called meristems.

In addition, many differentiated cells have the potential to both dedifferentiate and to reenter the cell cycle. There are also numerous examples of plant cell types that undergo endoreduplication, a process involving nuclear multiplication without cytokinesis. The study of plant cell cycle control genes is expected to contribute to the understanding of these unique phenomena. O. Shaul et al., *Regulation of Cell Division in Arabidopsis, Critical Reviews in Plant Sciences*, 15(2):97–112 (1996).

In spite of increases in yield and harvested area worldwide, it is predicted that over the next ten years, meeting the demand for corn will require an additional 20% increase over current production (Dowswell, C. R., Paliwal, R. L., Cantrell, R. P. 1996. Maize in the Third World, Westview Press, Boulder, Colo.).

The components most often associated with maize productivity are grain yield or whole-plant harvest for animal feed (in the forms of silage, fodder, or stover). Thus the relative growth of the vegetative or reproductive organs might be preferred, depending on the ultimate use of the crop. Whether the whole plant or the ear are harvested, overall yield will depend strongly on vigor and growth rate. It would therefore be valuable to develop new methods that contribute to the increase in crop yield.

SUMMARY OF THE INVENTION

It is an object of the present invention to provide methods for modulating cell division in a transgenic plant.

It is another object of the present invention to provide a method for influencing endoreduplication in a plant.

It is another object of the present invention to provide a method for increasing crop yield.

Therefore, in one aspect, the present invention provides a method for modulating endoreduplication comprising introducing into a plant cell a viral replicase nucleic acid, a viral replicase polypeptide or a functional derivative thereof.

In another aspect the present invention provides a method for increasing crop yield comprising introducing into a plant cell an isolated viral replicase polynucleotide or a functional variant thereof operably linked to a promoter driving expression in a plant.

BREIF DESCRIPTION OF THE DRAWINGS

FIG. 1 represents flow cytometric analysis of nuclei from plant tissue that has not been transformed with RepA and of nuclei from plant tissue transformed with RepA.

DETAILED DESCRIPTION OF THE INVENTION

Endoreduplication is a process involving one or more rounds of nuclear DNA replication in the absence of chromosomal and cellular division, leading to polyploidy. Evidence to date indicates that regulation of this process is similar in plants and animals; and that some factor (as yet unidentified) inhibits the kinase activity of the mitotic CDK/cyclin complex, while the cell cycle components that promote the G1/S phase transition and DNA replication continue to function (Grafi, G and B. A. Larkins, 1995, Endoreduplication in maize endosperm: Involvement of M phase-promoting factor inhibition and induction of S phase-related kinases, Science 269:1262–1264).

Endoreduplication is widespread among eukaryotes, being involved in numerous biological processes such as cell differentiation, cell expansion and accumulation of metabolites (see Trass et al., 1998, Endoreduplication and development: rule without dividing?, Current Opinion in Plant Biol. 1:498–503). In general, it is believed that endoreduplication provides a mechanism to accommodate cell enlargement, increases in organ mass, and maintain high metabolic activity associated with storage tissues. Thus it would be desirable to modulate this process through transgene manipulation. For example, enhancement of endoreduplication in the seed would result in increased seed size and biomass accumulation. Stimulating endoreduplication in vegetative portions of the plant could likewise result in larger organs and increased biomass.

Definitions

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, "viral replicase polypeptide" refers to polypeptides exhibiting retinoblastoma (Rb) binding function. The polypeptides include functional variants or derivatives of viral proteins, and/or functional homologues. The polypeptides include proteins encoded by genes in the viral genome that are commonly referred to as "replication proteins", "replication associated proteins", or "replication initiation proteins". The viral replicase polypeptide includes proteins from viruses in which all the "replication associated" or "replication" functions are encoded as a single protein, and those in which these functions are carried out by more than one protein, irrespective of whether proper or "inappropriate" splicing has occurred prior to translation (thus including both "Rep" and "RepA" forms).

As used herein, "viral replicase polynucleotide" refers to polynucleotides coding for a viral replicase polypeptide, including functional variants or functional derivatives of viral replicases, or functional homologs of characterized viral replicase polynucleotides.

As used herein, a "functional variant" or "functional derivative" are used interchangeably. As applied to polypeptides, the functional variant or derivative is a fragment, a modified polypeptide, or a synthetic polypeptide that stimulates DNA replication in a manner similar to the wild-type gene products, Rep and RepA.

As used herein, "polypeptide" and "protein" are used interchangeably and mean proteins, protein fragments, modified proteins, amino acid sequences and synthetic amino acid sequences. The polypeptide can be glycosylated or not.

As used herein, "plant" includes but is not limited to plant cells, plant tissue and plant seeds.

The present invention provides novel methods of using viral replicase polypeptides and polynucleotides. Included are methods for increasing crop yield and modulating endoreduplication.

Viral replicase polynucleotides, functional variants and/or functional homologs from any virus can be used in the methods of the invention as long as the expressed polypeptides exhibit Rb binding function, and/or stimulates DNA replication.

Examples of suitable plant viruses include wheat dwarf virus, maize streak virus, tobacco yellow dwarf virus, tomato golden mosaic virus, abutilon mosaic virus, cassava mosaic virus, beet curly top virus, bean dwarf mosaic virus, bean golden mosaic virus, chloris striate mosaic virus, digitaria streak virus, miscanthus streak virus, maize streak virus, panicum streak virus, potato yellow mosaic virus, squash leaf curl, sugarcane streak virus, tomato golden mosaic virus, tomato leaf curl virus, tomato mottle virus, tobacco yellow dwarf virus, tomato yellow leaf curl virus, African cassava mosaic virus, and the bean yellow dwarf virus.

Other viruses that bind Rb include animal DNA tumor viruses such as SV40 T antigen, adenovirus type 5 E1A and human papilloma virus type 16 E7 proteins. Replicase from the wheat dwarf virus has been sequenced and functionally characterized and is therefore preferred. Replicase binds to a well-characterized binding motif on the Rb protein (Xie et al., The EMBO Journal Vol. 14 No. 16 pp. 4073–4082,1995; Orozco et al., Journal of Biological Chemistry, Vol. 272, No. 15, pp. 9840–9846, 1997; Timmermans et al., Annual Review Plant Physiology. Plant Mol. Biol, 45:79–112, 1994; Stanley, Genetics and Development 3:91–96, 1996; Davies et al., *Geminivirus Genomes*, Chapter 2, and Gutierrez, Plant Biology 1:492–497, 1998). The disclosures of these items are incorporated herein by reference.

Viral nucleic acids useful in the present invention can be obtained using (a) standard recombinant methods, (b) synthetic techniques, or combinations thereof.

Viral replicase polynucleotides and functional variants useful in the invention can be obtained using primers that selectively hybridize under stringent conditions. Primers are generally at least 12 bases in length and can be as high as 200 bases, but will generally be from 15 to 75, preferably from 15 to 50. Functional fragments can be identified using a variety of techniques such as restriction analysis, Southern analysis, primer extension analysis, and DNA sequence analysis.

Variants of the nucleic acids can be obtained, for example, by oligonucleotide-directed mutagenesis, linker-scanning mutagenesis, mutagenesis using the polymerase chain reaction, and the like. See, for example, Ausubel, pages 8.0.3–8.5.9. Also, see generally, McPherson (ed.), *DIRECTED MUTAGENESIS: A Practical approach*, (IRL Press, 1991). Thus, the present invention also encompasses DNA molecules comprising nucleotide sequences that have substantial sequence similarity with the inventive sequences. Conservatively modified variants are preferred.

Nucleic acids produced by sequence shuffling of viral replicase polynucleotides can also be used. Sequence shuffling is described in PCT publication No. 96/19256. See also, Zhang, J.-H., et al. *Proc. Natl. Acad. Sci. USA* 94:4504–4509 (1997).

Also useful are 5' and/or 3' UTR regions for modulation of translation of heterologous coding sequences. Positive sequence motifs include translational initiation consensus sequences (Kozak, *Nucleic Acids Res.* 15:8125 (1987)) and the 7-methylguanosine cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)).

Further, the polypeptide-encoding segments of the polynucleotides can be modified to alter codon usage. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12: 387–395 (1984)) or MacVector 4.1 (Eastman Kodak Co., New Haven, Conn.).

For example, the polynucleotides can be optimized for enhanced or suppressed expression in plants. See, for example, EPA0359472; WO91116432; Perlak et al. (1991) *Proc. Natl. Acad. Sci. USA* 88:3324–3328; and Murray et al. (1989) *Nucleic Acids Res.* 17:477–498. In this manner, the genes can be synthesized utilizing species-preferred codons. See, for example, Murray et al. (1989) *Nucleic Acids Res.* 17:477–498, the disclosure of which is incorporated herein by reference.

The nucleic acids may conveniently comprise a multi-cloning site comprising one or more endonuclease restriction sites inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention.

The polynucleotides can be attached to a vector, adapter, promoter, transit peptide or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of such nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

To construct genomic libraries, large segments of genomic DNA are generated by random fragmentation. Examples of appropriate molecular biological techniques and instructions are found in Sambrook, et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The genomic library can be screened using a probe based upon the sequence of a nucleic acid used in the present invention. Those of skill in the art will appreciate that various degrees of stringency of hybridization can be employed in the assay; and either the hybridization or the wash medium can be stringent. The degree of stringency can be controlled by temperature, ionic strength, pH and the presence of a partially denaturing solvent such as formamide.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Preferably the hybridization is conducted under low stringency conditions which include hybridization with a buffer solution of 30% formamide, 1 M NaCl, 1% SDS (sodium dodecyl sulfate) at 37° C., and a wash in 1× to 2×SSC (20×SSC=3.0 M NaCl/0.3 M trisodium citrate) at 50° C. More preferably the hybridization is conducted under moderate stringency conditions which include hybridization in 40% formamide, 1 M NaCl, 1% SDS at 37° C., and a wash in 0.5× to 1×SSC at 55° C. Most preferably the hybridization is conducted under high stringency conditions which include hybridization in 50% formamide, 1 M NaCl, 1% SDS at 37° C., and a wash in 0.1×SSC at 60° C.

An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995). Often, cDNA libraries will be normalized to increase the representation of relatively rare cDNAs.

The nucleic acids can be amplified from nucleic acid samples using amplification techniques. For instance, polymerase chain reaction (PCR) technology can be used to amplify the sequences of polynucleotides of the present invention and related genes directly from genomic DNA or libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Examples of techniques useful for in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques,* 22(3): 481–486 (1997).

The nucleic acids can also be prepared by direct chemical synthesis by methods such as the phosphotriester method of Narang et al., *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.* 22: 1859–1862 (1981); the solid phase phosphoramidite triester method described by Beaucage and Caruthers, *Tetra. Letts.* 22(20): 1859–1862 (1981), e.g., using an automated synthesizer, e.g., as described in Needham-VanDevanter et al., *Nucleic Acids Res.*, 12: 6159–6168 (1984); and, the solid support method of U.S. Pat. No. 4,458,066.

Expression cassettes comprising the isolated viral replicase nucleic acids are also provided. An expression cassette will typically comprise a polynucleotide operably linked to transcriptional initiation regulatory sequences that will direct the transcription of the polynucleotide in the intended host cell, such as tissues of a transformed plant.

The construction of expression cassettes that can be employed in conjunction with the present invention is well known to those of skill in the art in light of the present disclosure. See, e.g., Sambrook, et al.; *Molecular Cloning: A Laboratory Manual*; Cold Spring Harbor, N.Y.; (1989); Gelvin, et al.; *Plant Molecular Biology Manual*; (1990); *Plant Biotechnology: Commercial Prospects and Problems*, eds. Prakash, et al.; Oxford & IBH Publishing Co.; New Delhi, India; (1993); and Heslot, et al.; *Molecular Biology and Genetic Engineering of Yeasts*; CRC Press, Inc., USA; (1992); each incorporated herein in its entirety by reference.

For example, plant expression cassettes may include (1) a viral replicase nucleic acid under the transcriptional control of 5' and 3' regulatory sequences and (2) a dominant selectable marker. Such plant expression cassettes may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill.

Examples of inducible promoters are the Adh1 promoter which is inducible by hypoxia or cold stress, the Hsp70 promoter which is inducible by heat stress, and the PPDK promoter which is inducible by light. Also useful are promoters which are chemically inducible.

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A., Martinez, M. C., Reina, M., Puigdomenech, P. and Palau, J.; Isolation and sequencing of a 28 kD glutelin-2 gene from maize: Common elements in the 5' flanking regions among zein and glutelin genes; Plant Sci. 47, 95–102 (1986) and Reina, M., Ponte, I., Guillen, P., Boronat, A. and Palau, J., Sequence analysis of a genomic clone encoding a Zc2 protein from Zea mays W64 A, Nucleic Acids Res. 18 (21), 6426 (1990). See the following site relating to the waxy promoter: Kloesgen, R. B., Gierl, A., Schwarz-Sommer, Z S. and Saedler, H., Molecular analysis of the waxy locus of Zea mays, Mol. Gen. Genet. 203, 237–244 (1986). Promoters that express in the embryo, pericarp, and endosperm are disclosed in U.S. applications Ser. Nos. 60/097,233 filed Aug. 20, 1998 and 60/098,230 filed Aug. 28, 1998. The disclosures each of these are incorporated herein by reference in their entirety.

Either heterologous or non-heterologous (i.e., endogenous) promoters can be employed to direct expression of the nucleic acids of the present invention. These promoters can also be used, for example, in expression cassettes to drive expression of antisense nucleic acids to reduce, increase, or alter concentration and/or composition of the proteins of the present invention in a desired tissue.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates. See for example Buchman and Berg, Mol. Cell Biol. 8:4395–4405 (1988); Callis et al., Genes Dev. 1:1183–1200 (1987). Use of maize introns Adh1-S intron 1, 2, and 6, the Bronze-1 intron are known in the art. See generally, The Maize Handbook, Chapter 116, Freeling and Walbot, Eds., Springer, New York (1994).

The vector comprising the polynucleotide sequences useful in the present invention will typically comprise a marker gene that confers a selectable phenotype on plant cells. Usually, the selectable marker gene will encode antibiotic or herbicide resistance. Suitable genes include those coding for resistance to the antibiotic spectinomycin or streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Suitable genes coding for resistance to herbicides include those which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), those which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Typical vectors useful for expression of nucleic acids in higher plants are well known in the art and include vectors derived from the tumor-inducing (Ti) plasmid of Agrobacterium tumefaciens described by Rogers et al., Meth. In Enzymol., 153:253–277 (1987). Exemplary A. tumefaciens vectors useful herein are plasmids pKYLX6 and pKYLX7 of Schardl et al., Gene, 61:1–11 (1987) and Berger et al., Proc. Natl. Acad. Sci. U.S.A., 86:8402–8406 (1989). Another useful vector herein is plasmid pBI101.2 that is available from Clontech Laboratories, Inc. (Palo Alto, Calif.). A variety of plant viruses that can be employed as vectors are known in the art and include cauliflower mosaic virus (CaMV), geminivirus, brome mosaic virus, and tobacco mosaic virus.

The viral replicase polynucleotide can be expressed in either sense or antisense orientation as desired. In plant cells, it has been shown that antisense RNA inhibits gene expression by preventing the accumulation of mRNA which encodes the enzyme of interest, see, e.g., Sheehy et al., Proc. Nat'l. Acad. Sci. (USA) 85:8805–8809 (1988); and Hiatt et al., U.S. Pat. No. 4,801,340.

Another method of suppression is sense suppression. For an example of the use of this method to modulate expression of endogenous genes see, Napoli et al., The Plant Cell 2:279–289 (1990) and U.S. Pat. No. 5,034,323. Another method of down-regulation of the protein involves using PEST sequences that provide a target for degradation of the protein.

Catalytic RNA molecules or ribozymes can also be used to inhibit expression of plant genes. The inclusion of ribozyme sequences within anti-sense RNAs confers RNA-cleaving activity upon them, thereby increasing the activity of the constructs. The design and use of target RNA-specific ribozymes is described in Haseloff et al., Nature 334:585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., Nucleic Acids Res (1986) 14:4065–4076, describe covalent bonding of a single-stranded DNA fragment with alkylating derivatives of nucleotides complementary to target sequences. A report of similar work by the same group is that by Knorre, D. G., et al., Biochimie (1985) 67:785–789. Iverson and Dervan also showed sequence-specific cleavage of single-stranded DNA mediated by incorporation of a modified nucleotide which was capable of activating cleavage (J Am Chem Soc (1987) 109:1241–1243). Meyer, R. B., et al., J. Am. Chem. Soc. (1989) 111:8517–8519, effect covalent crosslinking to a target nucleotide using an alkylating agent complementary to the single-stranded target nucleotide sequence. A photo-activated crosslinking to single-stranded oligonucleotides mediated by psoralen was disclosed by Lee, B. L., et al., Biochemistry (1988) 27:3197–3203. Use of crosslinking in triple-helix forming probes was also disclosed by Home, et al., J. Am. Chem. Soc. (1990) 112:2435–2437. Use of N4, N4-ethanocytosine as an alkylating agent to crosslink to single-stranded oligonucleotides has also been described by Webb and Matteucci, J Am Chem Soc (1986) 108:2764–2765; Nucleic Acids Res (1986) 14:7661–7674; Feteritz et al., J. Am. Chem. Soc. 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681941.

Proteins useful in the present invention include proteins derived from the native protein by deletion (so-called truncation), addition or substitution of one or more amino acids at one or more sites in the native protein. In constructing variants of the proteins of interest, modifications will be made such that variants continue to possess the desired activity.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488–492; Kunkel et al. (1987) *Methods Enzymol.* 154:367–382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

The present invention includes catalytically active polypeptides (i.e., enzymes). Catalytically active polypeptides will generally have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

The methods of the present invention can be used with any cell such as bacteria, yeast, insect, mammalian, or preferably plant cells. The transformed cells produce viral replicase protein.

Typically, an intermediate host cell will be used in the practice of this invention to increase the copy number of the cloning vector. With an increased copy number, the vector containing the nucleic acid of interest can be isolated in significant quantities for introduction into the desired plant cells. Host cells that can be used in the practice of this invention include prokaryotes, including bacterial hosts such as *Eschericia coli, Salmonella typhimurium*, and *Serratia marcescens*. Eukaryotic hosts such as yeast or filamentous fungi may also be used in this invention. It preferred to use plant promoters that do not cause expression of the polypeptide in bacteria.

Commonly used prokaryotic control sequences include promoters such as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Expression systems for expressing a protein of the present invention are available using Bacillus sp. and Salmonella (Palva, et al., *Gene* 22:229–235 (1983); Mosbach, et al., *Nature* 302:543–545 (1983)).

In some aspects of the invention, viral replicase proteins are introduced into a cell to modulate endoreduplication. Synthesis of heterologous proteins in yeast is well known. See Sherman, F., et al., *Methods in Yeast Genetics*, Cold Spring Harbor Laboratory (1982). Two widely utilized yeast for production of eukaryotic proteins are *Saccharomyces cerevisiae* and *Pichia pastors*. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

The protein can be isolated from yeast by lysing the cells and applying standard protein isolation techniques to the lysates. The monitoring of the purification process can be accomplished by using Western blot techniques or radioimmunoassay of other standard immunoassay techniques.

The proteins useful in the present invention can also be constructed using non-cellular synthetic methods. Techniques for solid phase synthesis are described by Barany and Merrifield, Solid-Phase Peptide Synthesis, pp. 3–284 in *The Peptides: Analysis, Synthesis, Biology. Vol. 2: Special Methods in Peptide Synthesis, Part A*.; Merrifield, et al., *J. Am. Chem. Soc.* 85:2149–2156 (1963), and Stewart et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide) are known to those of skill.

The proteins useful in this invention may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. Detection of the expressed protein is achieved by methods known in the art, for example, radioimmunoassays, Western blotting techniques or immunoprecipitation.

Expressing viral polypeptides is expected to increase crop yield. It is further expected that expression of viral replicase polynucleotide will increase endoreduplication. Endoreduplication is expected to increase the size of the seed, the size of the endosperm and the amount of protein in the seed. Similarly, endoreduplication is expected to increase the size of any plant cell, relative to neighboring non-endoreduplicated cells.

In a preferred embodiment, the invention can be practiced in a wide range of plants such as monocots and dicots. In a especially preferred embodiment, the methods of the present invention are employed in corn, soybean, sunflower, safflower, potato, tomato, sorghum, canola, wheat, alfalfa, cotton, rice, barley and millet.

The method of transformation/transfection is not critical to the invention; various methods of transformation or transfection are currently available. As newer methods are available to transform host cells they may be directly applied. Accordingly, a wide variety of methods have been developed to insert a DNA sequence into the genome of a host cell to obtain the transcription and/or translation of the sequence to effect phenotypic changes in the organism. Thus, any method that provides for efficient transformation/transfection may be employed.

A DNA sequence coding for the desired polynucleotide useful in the present invention, for example a cDNA, RNA or a genomic sequence, will be used to construct an expression cassette that can be introduced into the desired plant. Isolated nucleic acid acids of the present invention can be introduced into plants according techniques known in the art. Generally, expression cassettes as described above and suitable for transformation of plant cells are prepared.

Methods for transforming various host cells are disclosed in Klein et al. "Transformation of microbes, plants and animals by particle bombardment", Bio/Technol., New York, N.Y., Nature Publishing Company, March 1992, v. 10 (3) pp. 286–291.

Techniques for transforming a wide variety of higher plant species are well known and described in the technical, scientific, and patent literature. See, for example, Weising et al., *Ann. Rev. Genet*. 22: 421–477 (1988). For example, the DNA construct may be introduced directly into the genomic DNA of the plant cell using techniques such as electroporation, PEG-mediated transfection, particle bombardment, silicon fiber delivery, or microinjection of plant cell protoplasts or embryogenic callus. See, e.g., Tomes, et al., Direct DNA Transfer into Intact Plant Cells Via Microprojectile Bombardment. pp. 197–213 in Plant Cell, Tissue and Organ Culture, Fundamental Methods. eds. O. L. Gamborg and G. C. Phillips. Springer-Verlag Berlin Heidelberg New York, 1995. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using polyethylene glycol precipitation is described in Paszkowski et al., *Embo J*. 3:2717–2722 (1984). Electroporation techniques are described in Fromm et al., *Proc. Natl. Acad. Sci*. 82:5824 (1985). Ballistic transformation techniques are described in Klein et al., *Nature* 327: 70–73 (1987).

*Agrobacterium tumefaciens*-meditated transformation techniques are well described in the scientific literature. See, for example Horsch et al., *Science* 233:496–498 (1984), and Fraley et al., *Proc. Natl. Acad. Sci*. 80:4803 (1983). For instance, Agrobacterium transformation of maize is described in U.S. Pat. No. 5,550,318.

Other methods of transformation include (1) *Agrobacterium rhizogenes*-mediated transformation (see, e.g., Lichtenstein and Fuller In: Genetic Engineering, vol. 6, PWJ Rigby, Ed., London, Academic Press, 1987; and Lichtenstein, C. P., and Draper, J,. In: DNA Cloning, Vol. II, D. M. Glover, Ed., Oxford, IRI Press, 1985), Application PCT/US87/02512 (WO 88/02405 published Apr. 7,1988) describes the use of *A. rhizogenes* strain A4 and its Ri plasmid along with *A. tumefaciens* vectors pARC8 or pARC16 (2) liposome-mediated DNA uptake (see, e.g., Freeman et al., Plant Cell Physiol. 25:1353, 1984), (3) the vortexing method (see, e.g., Kindle, *Proc. Natl. Acad. Sci*., USA 87:1228, (1990).

DNA can also be introduced into plants by direct DNA transfer into pollen as described by Zhou et al., Methods in Enzymology, 101:433 (1983); D. Hess, Intern Rev. Cytol., 107:367 (1987); Luo et al., Plane Mol. Biol. Reporter, 6:165 (1988). Expression of polypeptide coding nucleic acids can be obtained by injection of the DNA into reproductive organs of a plant as described by Pena et al., Nature, 325:274 (1987). DNA can also be injected directly into the cells of immature embryos and the rehydration of desiccated embryos as described by Neuhaus et al., Theor. Appl. Genet., 75:30 (1987); and Benbrook et al., in Proceedings Bio Expo 1986, Butterworth, Stoneham, Mass., pp. 27–54 (1986).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of the present invention. For transformation and regeneration of maize see, Gordon-Kamm et al., *The Plant Cell*, 2:603–618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillan Publishing Company, New York, pp. 124–176 (1983); and Binding, *Regeneration of Plants, Plant Protoplasts*, CRC Press, Boca Raton, pp. 21–73 (1985).

Transformed plant cells, calli or explant can be cultured on regeneration medium in the dark for several weeks, generally about 1 to 3 weeks to allow the somatic embryos to mature. Preferred regeneration media include media containing MS salts, such as PHI-E and PHI-F media. The plant cells, calli or explant are then typically cultured on rooting medium in a light/dark cycle until shoots and roots develop. Methods for plant regeneration are known in the art and preferred methods are provided by Kamo et al., (*Bot. Gaz*. 146(3):324–334, 1985), West et al., (*The Plant Cell* 5:1361–1369, 1993), and Duncan et al. (*Planta* 165:322–332,1985).

Small plantlets can then be transferred to tubes containing rooting medium and allowed to grow and develop more roots for approximately another week. The plants can then be transplanted to soil mixture in pots in the greenhouse.

The regeneration of plants containing the foreign gene introduced by Agrobacterium can be achieved as described by Horsch et al., Science, 227:1229–1231 (1985) and Fraley et al., *Proc. Natl. Acad. Sci. U.S.A*., 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38:467–486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). For maize cell culture and regeneration see generally, *The Maize Handbook*, Freeling and Walbot, Eds., Springer, New York (1994); *Corn and Corn Improvement*, $3^{rd}$ edition, Sprague and Dudley Eds., American Society of Agronomy, Madison, Wis. (1988).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated viral replicase nucleic acid. Progeny and variants, and mutants of the regenerated plants are also included within the scope of the invention, provided that these parts comprise the introduced nucleic acid sequences.

Transgenic plants expressing a selectable marker can be screened for transmission of the viral replicase nucleic acid, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered cell division relative to a control plant (i.e., native, non-transgenic). Back-crossing to a parental plant and out-crossing with a non-transgenic plant are also contemplated.

Plants that can be used in the method of the invention vary broadly and include monocotyledonous and dicotyledonous plants. Preferred plants include corn, soybean, sunflower, sorghum, canola, wheat, alfalfa, cotton, rice, barley, potato, tomato, and millet.

Seeds derived from plants regenerated from transformed plant cells, plant parts or plant tissues, or progeny derived from the regenerated transformed plants, may be used directly as feed or food, or further processing may occur.

Expression of the viral replicase nucleic acids in plants, such as maize, is expected to enhance growth and biomass accumulation due to increased endoreduplication. Other more specialized applications exist for these nucleic acids at the whole plant level. It has been demonstrated that endoreduplication occurs in numerous cell types within plants, but this is particularly prevalent in maize endosperm, the primary seed storage tissue. Under the direction of endosperm-specific promoters, expression of viral replicase will further stimulate the process of endoreduplication.

The present invention will be further described by reference to the following detailed examples. It is understood, however, that there are many extensions, variations, and modifications on the basic theme of the present invention beyond that shown in the examples and description, which are within the spirit and scope of the present invention. All publications, patents, and patent applications cited herein are hereby incorporated by reference.

EXAMPLES

Example 1

Replicase Constructs

The replicase gene was obtained from Joachim Messing in the vector pWI-11, and was re-designated P100. Using P100 as the source, the replicase structural gene was cloned into an intermediate vector containing the 35S promoter and a 35S 3' sequence (for expression studies in dicotyledonous species, such as tobacco; designated P101 made in the Larkins Lab, Univ. of Arizona). From this intermediate plasmid, the RepA structural gene and the 35S 3' sequence were excised using the restriction enzyme NcoI and PstI, and cloned into P102 (gamma zein promoter::uidA::Gamma zein 3' region; after the removal of the GUS structural gene from P102 using NcoI/PstI). This resulted in a final construct containing an expression cassette with a maize gamma zein promoter sequence (GZ), the RepA coding sequence, a 35S terminator and a gamma zein 3' sequence (GZ'). Thus, the expression cassette had the configuration GZ::RepA::35S::GZ'P108.

A second plasmid, P107, contained genes conferring bailaphos resistance (bar gene) and expression of the visible marker, uidA, in the following expression cassettes; E35S::bar::pinII+UBI::uidA::pinII.

Example 2

RepA Modulates Endoreduplication in Cell Populations from Transgenic Plants.

Transformation of the Rep plasmid DNA, P108, into Hi-II germplasm followed a well-established bombardment transformation protocol used for introducing DNA into the scutellum of immature maize embryos (Songstad D. D. et al., In Vitro Cell Dev. Biol. Plant 32:179–183, 1996). It is noted that any suitable method of transformation can be used, such as Agrobacterium-mediated transformation and many other methods. Cells were transformed by culturing maize immature embryos (approximately 1.5–2.0 mm in length) onto medium containing N6 salts, Erikkson's vitamins, 0.69 g/l proline, 2 mg/) 2,4-D and 3% sucrose. After 4–5 days of incubation in the dark at 28° C., embryos were removed from the first medium and cultured onto similar medium containing 12% sucrose. Embryos were allowed to acclimate to this medium for 3 h prior to transformation. The scutellar surface of the immature embryos was targeted using particle bombardment with either the E35S::bar::pinII+IBU::GUS::pinII plasmid (P107; control treatment) or with a combination of P107+the replicase plasmid, P108. Embryos were transformed using the PDS-1000 Helium Gun from Bio-Rad at one shot per sample using 650 PSI rupture disks. DNA delivered per shot averaged at 0.0667 g. An equal number of embryos per ear were bombarded with either the control DNA mixture or the Rep/GFP DNA mixture. Following bombardment, all embryos were maintained on 560 L medium (N6 salts, Eriksson's vitamins, 0.5 mg/l thiamine, 20 g/l sucrose, 1 mg/l 2,4-D, 2.88 g/l proline, 2.0 g/l gelrite, and 8.5 mg/l silver nitrate). After 2–7 days post-bombardment, all the embryos from both treatments were transferred onto N6-based medium containing 3 mg/l bialaphos (Pioneer 560P medium described above, with no proline and with 3 mg/l bialaphos). Plates were maintained at 28° C. in the dark and were observed for colony recovery with transfers to fresh medium occurring every two weeks. After 6 weeks, stable transformants were scored, and expression of a second marker gene (GUS) was used to confirm the transgenic nature of the callus. Transgenic calli expressing bar and GUS alone (from the control treatment), or transgenic calli expressing bar, GUS and RepA were regenerated. Transformed plant cells, calli or explants were cultured on regeneration medium in the dark for several weeks, generally about 1 to 3 weeks to allow the somatic embryos to mature. Preferred regeneration media included media containing MS salts, such as PHI-M medium, which contains MS salts, MS vitamins, 100 mg/l myo-inositol, 0.5 mg/l zeatin, 1 mg/l IAA, 10–7 M ABA, 60 g/l sucrose, 3 g/l gelrite, and 3 mg/l bialaphos, pH 5.6. The plant cells, calli or explants were then typically cultured on rooting medium (for example, PHI-E, containing MS salts, MS vitamins, 100 mg/l myo-inositol, 40 g/l sucrose, and 1.5 g/l gelrite, pH 5.6) in a light/dark cycle (16 hours light, 100 $\mu$E; 8 hours dark) until shoots and roots developed. When plants were approximately 10 cm in length, they were transferred to soil in the greenhouse. When plants were 1 to 1.5 meters tall, leaf samples were harvested for isolation of nuclei. For extraction of nuclei, callus was macerated with a straight-edge razor blade in a buffer consisting of 45 mM CgCL$_2$, 30 mM sodium citrate, 20 mM MOPS buffer, 0.1% v/v Triton X 100. For each callus event sampled, tissue (approximately 1 cm$^3$) was transferred to a Petri dish, and macerated with a small volume of the chopping buffer. The resulting suspension was then passed sequentially through 60 um and 20 um sieves and transferred to a 15 ml centrifuge tube on ice. Tubes were centrifuged at 100 g for 5 minutes at 40° C. The supernatant was decanted, the pellets resuspended in ~750 $\mu$l of staining solution (100 $\mu$g/ml propidium iodide in chopping buffer) and transferred to tubes for analysis in the flow cytometer. Stained nuclei were analyzed on an EPICS-XL-MCL flow cytometer using a 488 nm argon laser for excitation and measuring emission from 500–550 nm. Collecting propidium iodide fluorescence measurements on a per-nucleus basis (equivalent to the DNA content per nucleus) permitted the assessment of cell cycle stages in the callus-cell population.

The cell cycle profile from leaf nuclei of non-transformed plants was typical of maize leaf cell populations, with a predominant G1 peak (approximately 80%), a low percentage of S phase (8%), and a low percentage of G2 (approximately 12%). In a RepA-treated regenerated plant, the cell cycle profile was dramatically shifted. The proportion of cells in the peak that normally corresponds to a diploid G2 phase (4C DNA content) increased, and a new peak corresponding to cells with an unusually high DNA content has become readily apparent (see FIG. 1). This third peak appeared to represent tetraploid cells in the G2 phase of the cell cycle, with an 8C DNA content. Thus, the intermediate peak contained a mixture of diploid G2 cells and tetraploid G1 (both 4C DNA content and therefore these peaks overlap and are indistinguishable in this assay). This evidence is consistent with a stimulation of endoreduplicative cycle in leaf cells. While some small degree of endoreduplication normally occurs in specialized leaf cells (i.e. some epidermal cells and trichomes), the level of overall polyploidy observed in this experiment due to endoreduplication is not typical, and thus clearly indicates a phenotype due to expression of the RepA protein.

Example 3

Control of RepA Gene expression using Tissue-specific or Cell-specific Promoters Results in Differential Modulation of Endoreduplication RepA gene expression using tissue-specific or cell-specific promoters modulate endoreduplication in the expressing tissues or cells. For example, using a seed-specific promoter will stimulate endoreduplication and result in increased seed biomass. Expression of RepA genes in other cell types and/or at different stages of development is similarly expected to modulate endoreduplication.

Inducible Expression

The RepA gene can also be cloned into a cassette with an inducible promoter such as the benzenesulfonamide-inducible promoter. The expression vector is co-introduced into plant cells and after selection on bialaphos, the transformed cells are exposed to the safener (inducer). This chemical induction of RepA expression results in stimulated G1/S transition and enhanced endoreduplication rates. The cells are screened for the presence of RepA RNA by northern blot, or RT-PCR (using transgene specific probes/oligo pairs), for RepA-encoded protein using RepA-specific antibodies in Westerns or using hybridization. Increased levels of endoreduplication can be monitored using flow cytometry methods.

What is claimed is:

1. A method for increasing endoreduplication in a plant comprising stably transforming a plant cell with an isolated wheat dwarf virus RepA polynucleotide operably linked to a promoter capable of driving expression in the plant cell, growing the plant cell to produce a transformed plant, wherein the transformed plant exhibits increased endoreduplication compared to a corresponding non-transformed plant.

2. The method of claim 1 wherein the plant cell is from a monocot or a dicot plant.

3. The method of claim 2 wherein the plant cell is from corn, soybean, sunflower, sorghum, canola, wheat, alfalfa. cotton, rice, barley, potato, tomato, and millet.

4. The method of claim 3 wherein the plant is corn or soybean.

5. The method of claim 1 wherein the promoter is inducible, or regulated in a tissue specific manner developmentally or temporally regulated.

* * * * *